United States Patent
Ijiro et al.

[11] Patent Number: 6,020,131
[45] Date of Patent: Feb. 1, 2000

[54] NUCLEIC ACID POLYMER/INTERCALATOR MONOLAYER AND METHODS OF USING AND MAKING THEREOF

[75] Inventors: Kunihara Ijiro; Masatsugu Shimomura, both of Hokkaido, Japan

[73] Assignee: Research Development Corporation of Japan, Saitama, Japan

[21] Appl. No.: 08/966,403

[22] Filed: Nov. 7, 1997

Related U.S. Application Data

[62] Division of application No. 08/595,206, Feb. 1, 1996, Pat. No. 5,871,915.

[30] Foreign Application Priority Data

Mar. 13, 1995 [JP] Japan ................................. 7-052174

[51] Int. Cl.[7] .......................... C12Q 1/68; C07D 219/00; C07H 21/04; G01N 33/566
[52] U.S. Cl. .............................. 435/6; 546/102; 546/104; 546/105; 536/22.1; 536/23.1; 536/24.3; 436/501; 436/518; 436/536
[58] Field of Search ................................ 435/6; 546/102, 546/104, 105; 536/22.1, 23.1, 24.3; 436/501, 518, 536

[56] References Cited

U.S. PATENT DOCUMENTS

| | | | |
|---|---|---|---|
| 4,563,417 | 1/1986 | Albarella et al. | 435/6 |
| 5,194,393 | 3/1993 | Hugl et al. | 436/525 |

OTHER PUBLICATIONS

Masaru Tanaka et al., "Preparation of Nucleic DNA Monolayer Complex by Polyionic Complex Process", Hokkaido University regional winter meeting of the Japanese Chemical Society held Feb. 2, 1995. (with English Abstract).

Kajiyama et al., "Effect of Polycation in Subphase on Aggregation Structure of Monolayer and Langmuir–Blodgett Film of Anionic Amphiphile" Langmuir, vol. 9, pp. 760–765, 1993.

Uhlmann et al., "Antisense Oligonucleotides: A New Therapeutic Principle" Chemical Review, vol. 90, p. 543, 1990.

Yamagishi et al. Effects of an aliphatic tail on the interactions of an ionic dye and a polyelectrolyte. The system of N–alylated acridine orange and poly(styrenesulfonic acid). J. Phys. Chem., vol. 85, pp. 2129–2134, 1981.

*Primary Examiner*—Jezia Riley
*Attorney, Agent, or Firm*—Wenderoth, Lind & Ponack, L.L.P.

[57] ABSTRACT

The present invention has an object to provide an easy method for detecting a nucleic acid polymer in aqueous phase.

The present invention provides a method for detecting the amount of nucleic acid polymer, which comprises the steps of modifying an intercalator to be amphiphilic by using a hydrophobic group, spreading the amphiphilic intercalator on an aqueous solution containing a nucleic acid polymer to form a monolayer of said nucleic acid polymer and said amphiphilic intercalator at the gas-water interface, and measuring surface pressures per unit area of said monolayer.

18 Claims, 10 Drawing Sheets

NUCLEIC ACID POLYMER/INTERCALATOR MONOLAYER AND METHODS OF USING AND MAKING THEREOF

This is a divisional application of Ser. No. 08/595,206 filed Feb. 1, 1996 now U.S. Pat. No. 5,871,915.

BACKGROUND OF THE INVENTION

1. Field of the Invention

The present invention relates to a method for detecting a nucleic acid polymer. More particularly, the present invention relates to a method which permits easy detection of an amount of a nucleic acid polymer in a sample, detection of hybridization, if any, of a probe and a nucleic acid polymer, identification of a base sequence of a nucleic acid polymer, a method for causing two-dimensional orientation of a nucleic acid polymer at the gas-water interface, and further, a novel amphiphilic intercalator used in these methods.

2. Description of Related Art

Diverse and various biological functions observed in cells are effectively expressed by regular orientation of biomolecules. For nucleic acid polymers (DNA, RNA) which code genetic information of an organism, however, the effect of an orientation thereof on expression of biological functions has almost never been studied. One of the reasons is that means to control in vitro the orientation of a nucleic acid polymer has not as yet been established.

As a method for retrieving a target gene sequence in a nucleic acid polymer, or for determining similarities and differences or homology of a plurality of nucleic acid polymers, on the other hand, it is conventionally known that the hybridization method using, as a probe, a single-stranded nucleic acid polymer (DNA or RNA) complementary with a portion of sequence of a target nucleic acid polymer. More specifically, the conventional hybridization method comprises the steps of fixing a single-stranded target nucleic acid polymer onto a nitrocellulose membrane or a nylon membrane, and adding an aqueous solution of a probe nucleic acid polymer labelled with a radioisotope or an enzyme onto the membrane. When the probe nucleic acid polymer is hybridized with the target nucleic acid polymer, only the hybridized probe nucleic acid polymer remains on the membrane after washing. Presence of a searched sequence in the target nucleic acid can be determined by detecting radioactivity from the radioisotope labelled on the probe nucleic acid polymer, or chemiluminescence or color of precipitate produced by the enzyme.

In order to handle a radioisotope, however, it is necessary to acquire a special license, so that this technique is not popularly accepted. Labelling a single-stranded probe nucleic acid polymer with an enzyme requires much costs and labor.

A nucleic acid polymer such as genomic DNA existent in chromosome has a double helix structure comprising complementary base pairs (adenine/thymine and cytosine/guanine for DNA, and adenine/uridine, cytosine/inosine and cytosine/guanine for RNA). For identifying differences in the base sequence between two different nucleic acid polymers, for example, formation of a triple helix has been believed to be effective. However, because of the difficulty to detect formation of a triple helix, this method has not as yet been put to practical use.

Among properties of DNA or RNA as a nucleic acid polymer, there is known an intercalation phenomenon in which a cationic pigment is inserted between neighboring base pairs. However, detection of a nucleic acid polymer (content, hybridization, identification of base sequence, etc.) by the use of this phenomenon has not as yet been conducted.

SUMMARY OF THE INVENTION

The present invention has as an object to provide a method for detecting an amount of a nucleic acid polymer in an aqueous solution and the presence of hybridization of nucleic acid polymer/probe by the utilization of interaction between a pigment (intercalator) and the nucleic acid polymer, and a method for identifying the base sequence of the nucleic acid polymer.

More specifically, the first invention provided by the present invention is a method for detecting an amount of nucleic acid polymer, which comprises the steps of modifying an intercalator to be amphiphilic by using a hydrophobic group, spreading the amphiphilic intercalator on an aqueous solution containing a nucleic acid polymer to form a monolayer of said nucleic acid polymer and said amphiphilic intercalator, and measuring surface pressure per unit area of said monolayer at the gas-water interface.

The second invention relates to a method for detecting the presence of hybridization of a probe nucleic acid polymer and a target nucleic acid polymer, which comprises the steps of modifying an intercalator to be amphiphilic by using a hydrophobic group, spreading the amphiphilic intercalator on an aqueous solution containing a single-stranded probe nucleic acid polymer to form a monolayer of said probe nucleic acid polymer and said amphiphilic intercalator at the gas-water interface, measuring a surface pressure-area isotherm of said monolayer, then measuring a surface pressure-area isotherm of said monolayer after addition of a single-stranded target nucleic acid polymer to the aqueous solution, and comparing the two surface pressure-area isotherms.

The third invention relates to a method for identifying a base sequence of a nucleic acid polymer, which comprises the steps of modifying an intercalator to be amphiphilic by using a hydrophobic group, spreading the amphiphilic intercalator on an aqueous solution containing a nucleic acid polymer to form a monolayer of the nucleic acid polymer and the amphiphilic intercalator at the gas-water interface, and measuring surface pressure-area isotherm of said monolayer.

The present invention has another object to provide a method for causing two-dimensional orientation of a nucleic acid polymer at the gas-water interface.

More specifically, the fourth invention is a method for orientating nucleic acid polymers at the gas-water interface, which comprises the step of modifying an intercalator to be amphiphilic by using a hydrophobic group, spreading the amphiphilic intercalator on an aqueous solution containing nucleic acid polymers to form a monolayer of said nucleic acid polymers and said amphiphilic intercalator.

Furthermore, the present invention provides an intercalator modified to be amphiphilic by using a hydrophobic group and a nucleic acid polymer/intercalator monolayer comprising this intercalator and the nucleic acid polymer.

DETAILED DESCRIPTION OF THE INVENTION

The present invention permits detection of a nucleic acid polymer by utilizing intercalation of a pigment, forming a monolayer of an intercalator and a nucleic acid polymer at the gas-water interface, and measuring a surface pressure of this monolayer. The method is characterized in that a surface active pigment modified by a hydrophobic group into an amphiphilic one is used as the intercalator. The individual detection methods are described below in detail.

<A> Detection of Nucleic Acid Polymer Amount:

First, a nucleic acid polymer (single-stranded or double-stranded DNA or RNA) is added into an aqueous subphase of an ordinary surface pressure-area isotherm measuring apparatus. A monolayer is formed by spreading the surface-active intercalator of the present invention at the gas-water interface. More specifically, since this intercalator has a positive charge, it forms a polyion complex with the nucleic acid polymer having a negative charge at the gas-water interface, thus forming a monolayer. The surface pressure of this monolayer varies, depending upon the amount of nucleic acid polymer coupled with the intercalator. By measuring the surface pressure thereof per unit area (area occupied by the monolayer), therefore, it is possible to detect the amount of the nucleic acid polymer in the aqueous solution. More particularly, the amount can be detected by determining the difference between the measured surface pressure and the surface pressure of pure water not containing a nucleic acid polymer. By previously preparing a calibration curve of differences in surface pressure by the use of nucleic acid polymer aqueous solutions having various known concentrations, furthermore, it is possible to easily detect the amount of a nucleic acid polymer of an unknown concentration.

Figure 1:
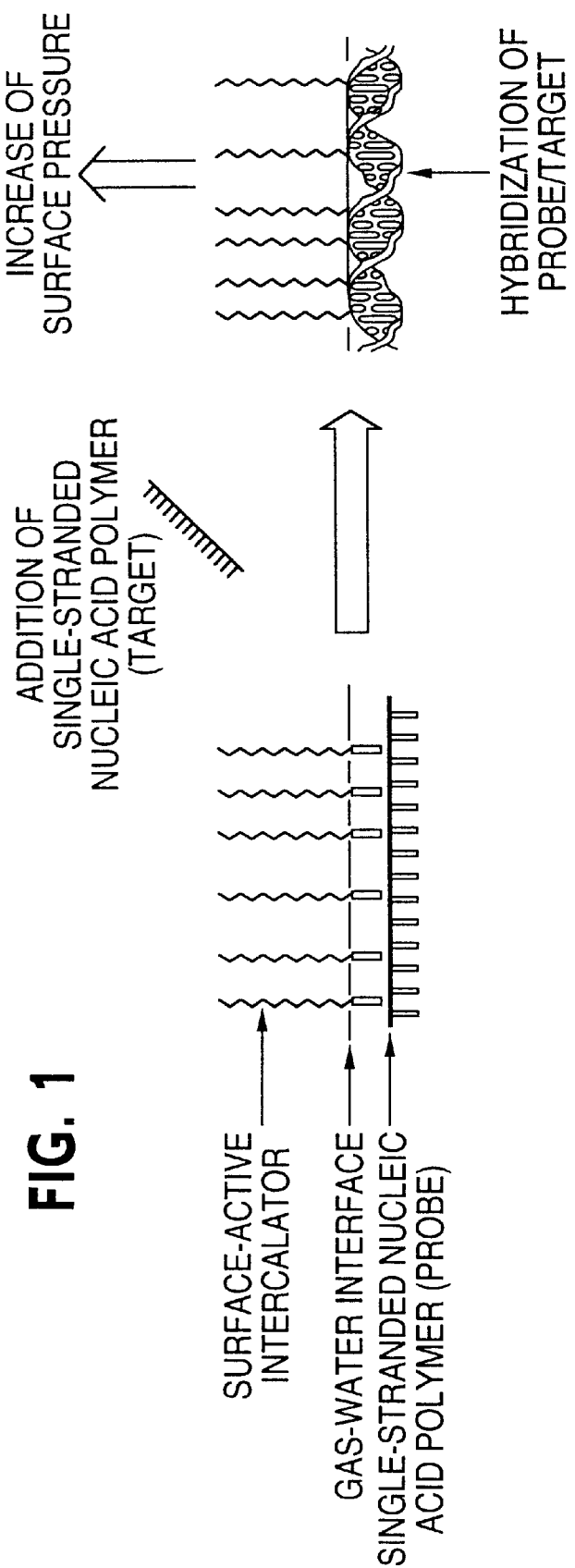
FIG. 1 is a schematic representation illustrating a method for detecting the presence of hybridization in the present invention.

<B> Hybridization:

First, as shown in FIG. 1, a single-stranded probe nucleic acid polymer (DNA or RNA) is added into an aqueous subphase of an ordinary surface pressure-area isotherm measuring apparatus. A monolayer is formed by spreading the surface-active intercalator solution onto the gas-water interface thereof. At this point, as the intercalator has a positive charge, it forms a polyion complex with the single-stranded nucleic acid polymer having a negative charge at the gas-water interface, thus forming a monolayer. The surface pressure-area isotherm ($\pi$-A isotherm) of the thus formed monolayer is measured. Then a single-stranded nucleic acid polymer which may have a target sequence to be detected is added to the aqueous subphase. When the target nucleic acid polymer has a base sequence complementary with the probe, the single-stranded probe nucleic acid polymer having formed the polyion complex with the intercalator is hybridized with the single-stranded target nucleic acid polymer, thus forming a polyion complex comprising the intercalator and double-stranded probe/target nucleic acid polymer at the gas-water interface. Because the pigment portion of the intercalator is inserted between base pairs of the double-stranded probe/target nucleic acid polymer, there is created a surface pressure-area isotherm different from that before hybridization. This difference in the surface pressure-area isotherm makes it possible to detect the presence of hybridization.

Figure 2:
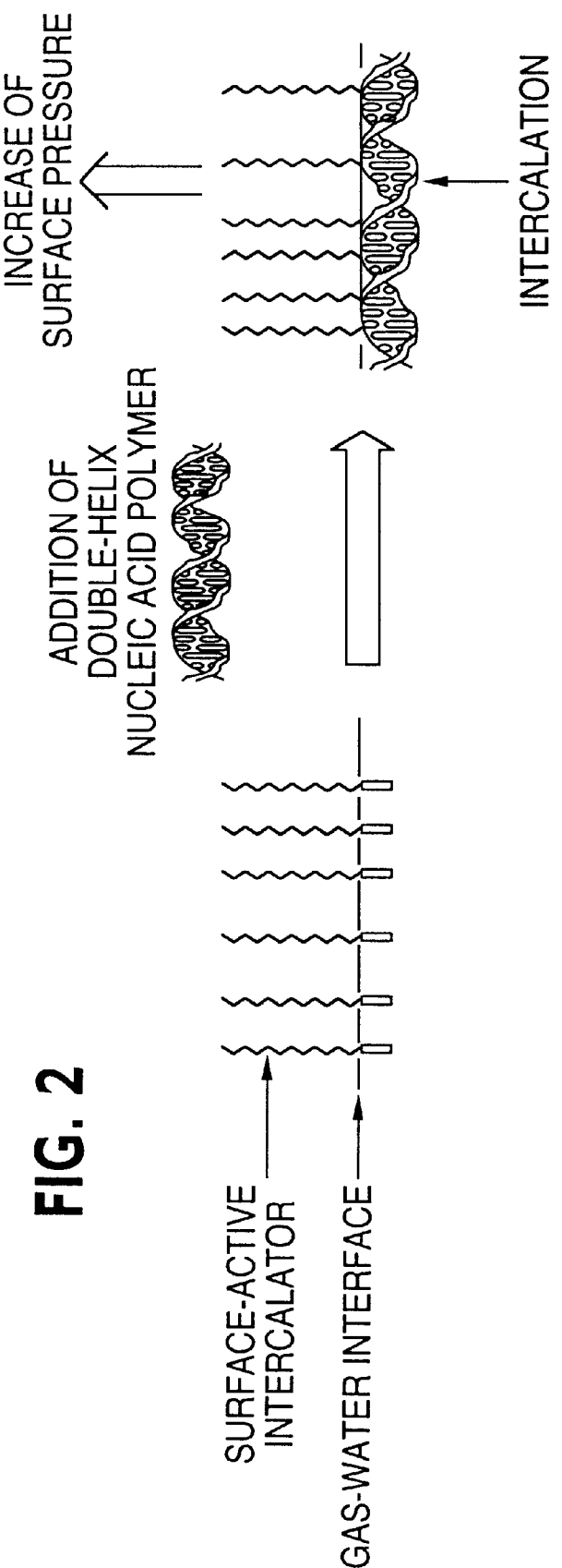
FIG. 2 is a schematic representation illustrating a method for identifying a base sequence in the present invention.

<C> Identification of Difference Between Base Sequences of Nucleic Acid Polymer:

As shown in FIG. 2, for example, an aqueous solution of a target double helix nucleic acid polymer (DNA or RNA) is added into the aqueous subphase of an ordinary surface pressure-area isotherm measuring apparatus. A monolayer is formed by spreading a surface active intercalator solution at the gas-water interface thereof. At this point, since the surface-active intercalator has a positive charge, it forms a polyion complex at the gas-water interface with the nucleic acid polymer having a negative charge, thus forming a monolayer. Further, the pigment intercalator portion intercalates with the double helix nucleic acid polymer. The surface pressure-area isotherm thereof is measured. Because the surface pressure-area isotherm largely depends upon the base sequence of the double helix nucleic acid polymer, it is possible to identify, from the surface pressure-area isotherm, the kind of base sequence of a nucleic acid polymer existent in the aqueous subphase. That is, the base sequence can be identified by previously preparing surface pressure-area isotherms for nucleic acid polymers having various known sequences, and comparing a tested sequence with these isotherms.

<D> Method for Causing Two-dimensional Orientation of Nucleic Acid Polymer:

First, an aqueous solution of a nucleic acid polymer (single-stranded or double-stranded DNA or RNA) is added into an aqueous subphase of an ordinary surface pressure-area isotherm measuring apparatus. A monolayer is formed by spreading a solution of the surface-active intercalator of the present invention at the gas-water interface thereof. Because this intercalator has a positive charge, it forms a polyion complex at the gas-water interface with the nucleic acid polymer having a negative charge, thus forming a monolayer. By compressing or dispersing this monolayer, for example, while controlling the surface pressure of the monolayer, it is possible to control orientation of the nucleic acid polymer coupled with the intercalator.

Now, the surface-active pigment intercalator used in the method of the present invention will be described in detail below.

Intercalation is observed in pigments such as acridine orange and ethidium bromide. In the present invention which utilizes formation of a complex with a nucleic acid, any of these various pigment intercalators including these conventional ones is modified by a hydrophobic group to impart an amphiphilic surface activity.

A typical hydrophobic group used here is alkyl group. The present invention proposes, as a more preferable one, a compound modified by $C_nH_{2n+1}(n \geq 13)$ alkyl group. For example, surface-active intercalators of the following formulae, available by modifying acridine orange with octadecyl group are provided:

FORMULA 1

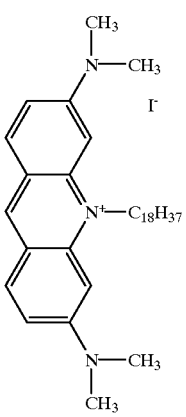

FORMULA 2

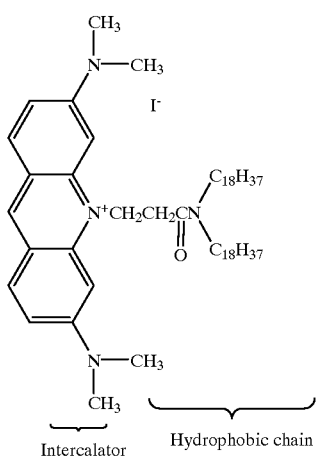

The compounds expressed by Formulae 1 and 2 are surface-active intercalators so far unknown, which can easily be synthesized by reacting an octadecyl iodine or a derivative thereof with the compound skeleton of acridine orange. The compound of Formula 1 is a surface-active intercalator having one hydrophobic chain, and the compound of Formula 1 is a surface-active intercalator having two hydrophobic chains.

These compounds will be described below by means of Examples of the present invention.

EXAMPLE 1

The presence of hybridization was measured with the use of the compound of Formula 1 above. The compound had the following properties:

(1) recrystallization from benzene:rubiginous imbricate crystal;

(2) melting point: 202.5~204.5° C.;

(3) TLC:Rf=0.5 (chloroform/methanol=9/1+some drops of acetic acid).

In addition, the elemental analysis of this compound is that of Table 1.

TABLE 1

|  | C | H | N | I |
|---|---|---|---|---|
| Theoretical Value (%) | 65.10 | 8.74 | 6.51 | 19.65 |
| Analytical Value (%) | 63.81 | 8.47 | 6.70 | 21.26 |

Figure 3:
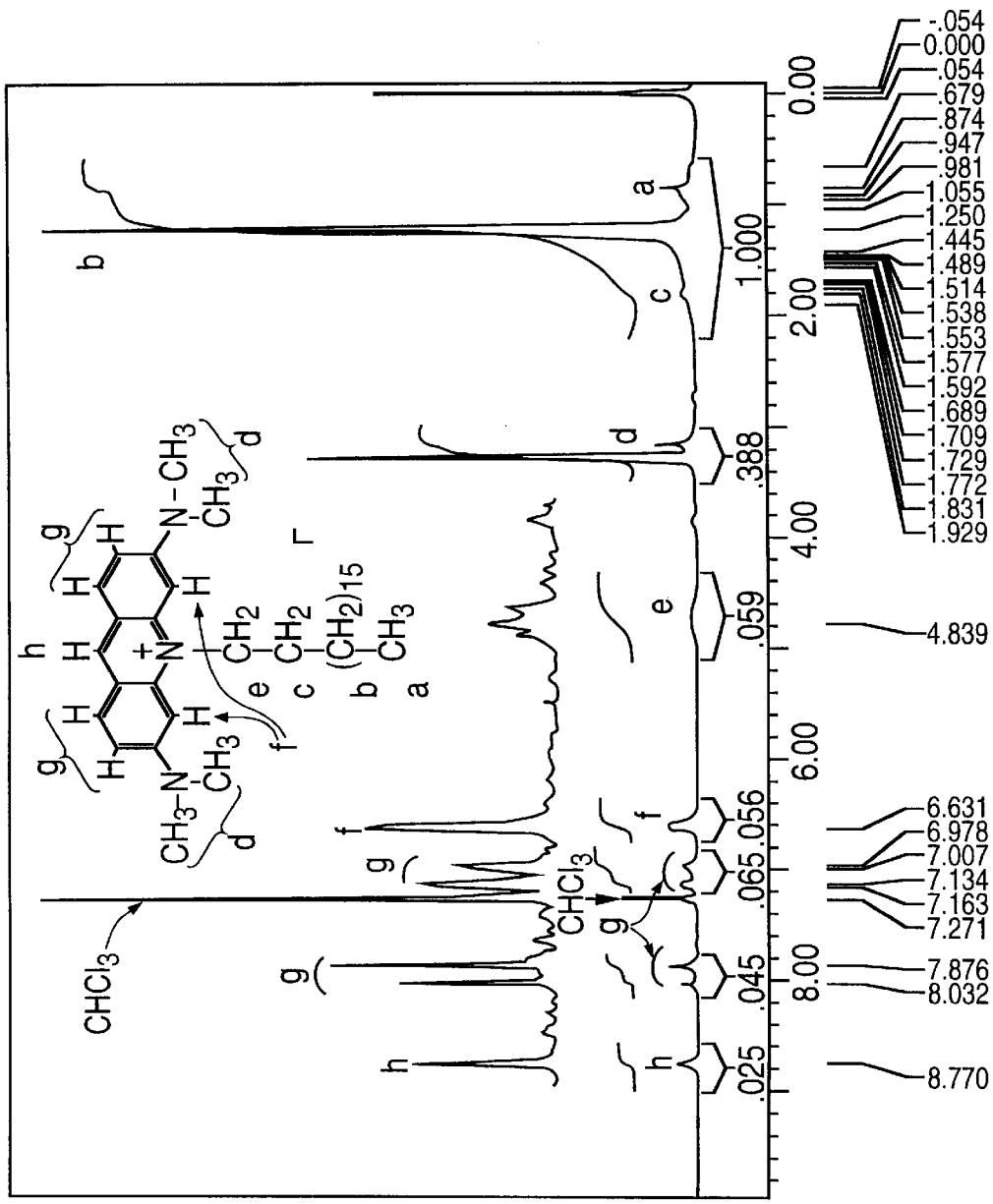
FIG. 3 is an NMR spectrum of an intercalator (Formula 1) of the present invention and FIG. 4 is an IR spectrum thereof.
Figure 4:
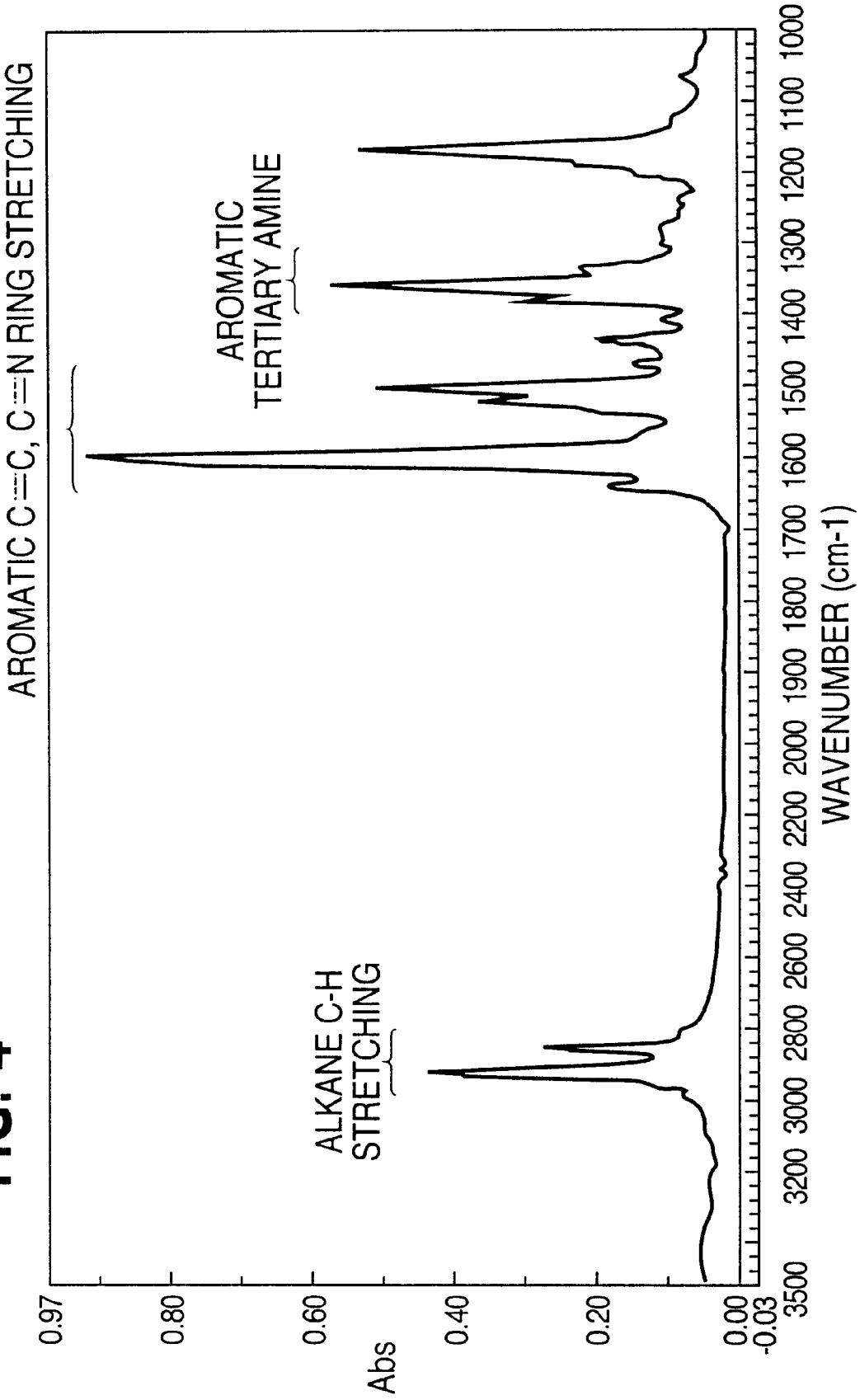

MHR and IR data are shown in FIGS. 3 and 4.

Figure 5:
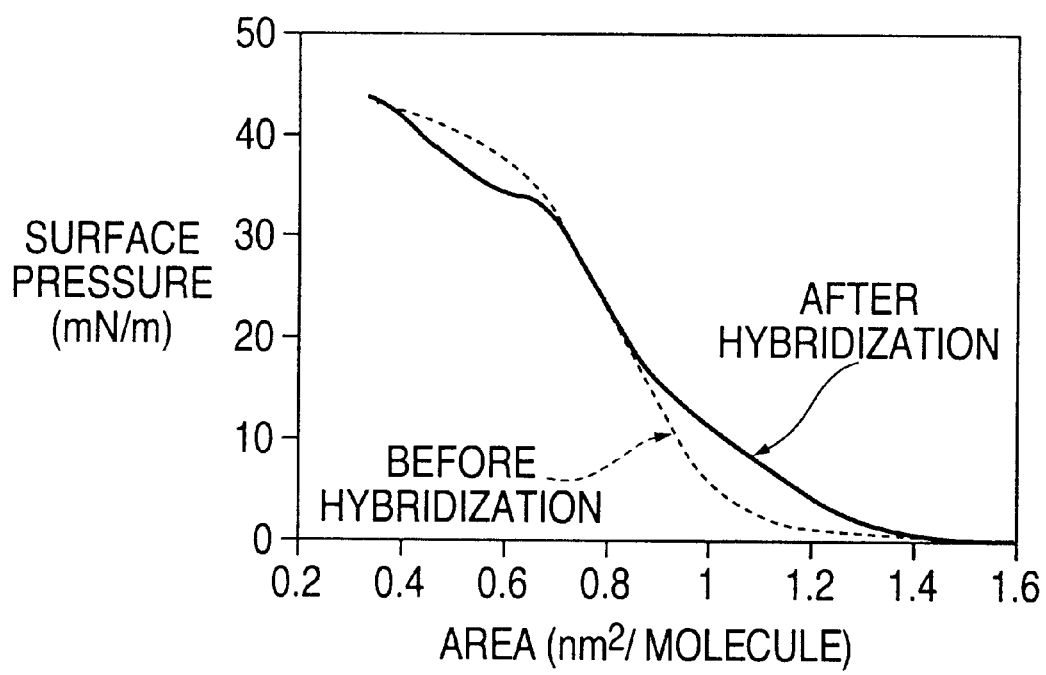
FIG. 5 illustrates the difference in surface pressure-area isotherms between the presence and absence of hybridization.

The results of actual measurement of surface pressure-area isotherms for this compound are shown in FIG. 5. The subphase exchange type film balance controlled by a microprocessor (made by USI Systems Company) was employed for measurement of surface pressure-area isotherms. With a trough area of 220×100 $mm^2$, the surface pressure was measured with the use of filter paper (1 cm×1 cm) by the Wilhelmy method. While measuring surface pressure-area isotherms, temperature of the aqueous subphase was kept constant (20° C. by means of a circulator. A chloroform (special class) solution of a surface-active intercalator (10 mg/10 ml) in an amount of 15 $\mu$l was spreaded on the aqueous subphase containing a nucleic acid polymer to measure surface pressure-area isotherms at a compression rate of 0.04 $nm^2$/min/molecule.

In addition, the following conditions were adopted:

Polyadenylic acid concentration of aqueous subphase:
10 mg/1000 ml (pure water), pH: 5.6

Inverted polyuridylic acid concentration:
10 mg/1000 ml (pure water), pH: 5.6.

As a model of single-stranded nucleic acid polymer, polyadenine was used, and as a model of single-stranded target nucleic acid polymer, complementary polyuridine was employed. A large change in surface pressure-area isotherms was confirmed by the addition of polyuridine to the aqueous subphase.

EXAMPLE 2

A base sequence of DNA was identified by the use of the compound of Formula 2 above. The compound was purified from silica gel column by using a solution of chloroform/methanol (=95/5) as an eluate, and TLC:Rf=0.5 (chloroform/methanol=9/1+some drops of acetic acid).

Figure 6:
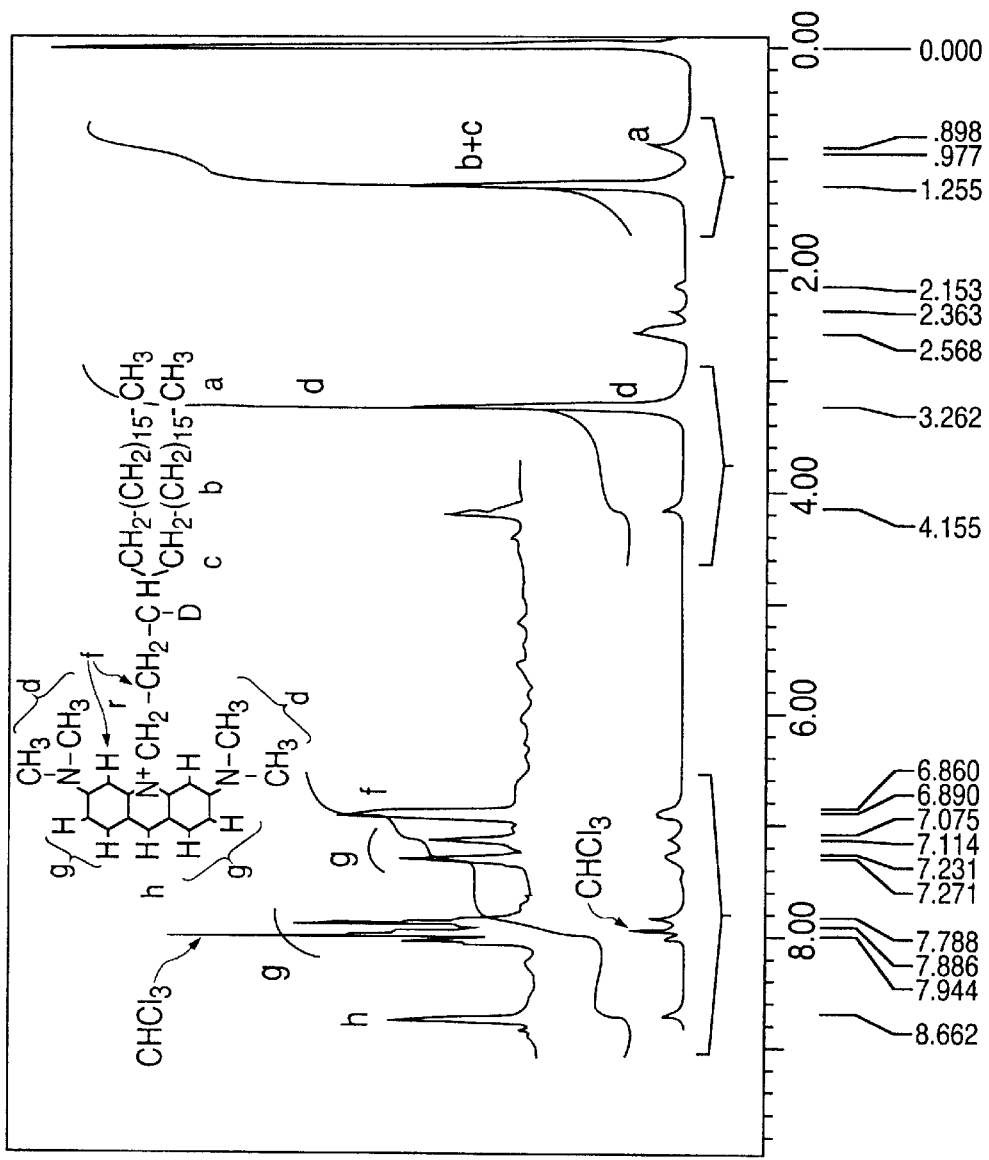
FIG. 6 is an NMR spectrum of another intercalator (Formula 2) of the present invention.

NMR data are shown in FIG. 6.

Figure 7:
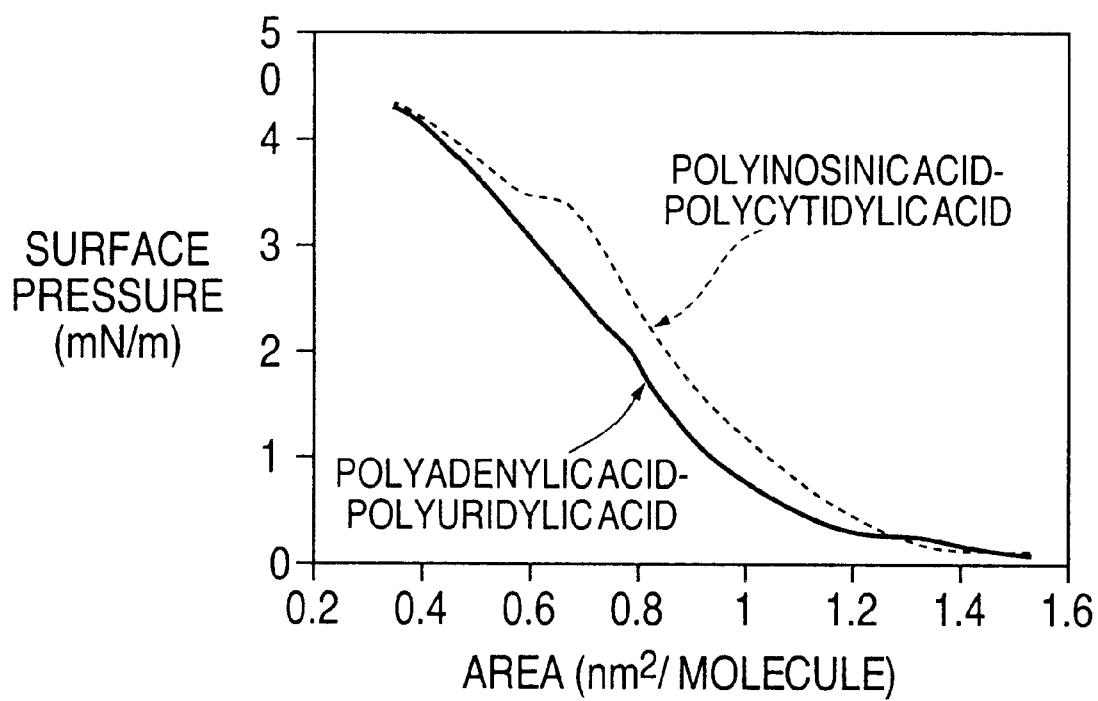
FIG. 7 illustrates the difference in surface pressure-area isotherms between different base sequences.

The results of actual measurement of surface pressure-area isotherms for this compound are shown in FIG. 7.

Measurement was carried out in the same manner as in Example 1, with other conditions including a concentration of the double helix nucleic acid polymer in the aqueous subphase of 10 mg/1000 ml (pure water) and a pH of 5.6. The graph is a surface pressure-area isotherm for the case where polyadenylic acid-polyuridylic acid and polyinosinic acid-polycytidylic acid were present in the aqueous subphase as models of double helix nucleic acid polymer.

More specifically, as shown in FIG. 7, the base sequence can be identified from a change in the surface pressure by adding a double helix nucleic acid polymer to the aqueous subphase if the gas-water interface has a constant surface area.

EXAMPLE 3

An aqueous solution was prepared by dissolving a double helix DNA (extracted from salmon spermatozoon) in pure water, to a DNA concentration within a range of from 0.01 to 100 mg/1000 ml and a pH of 5.6. A chloroform solution of the surface-active intercalator of Formula 1 was spreaded onto the gas-water interface of this aqueous solution, and the surface pressure-area isotherm was measured by the same method under the same conditions as in Example 1. The surface pressure was measured with a molecule-occupying area of 0.8 nm²/molecule, and on the other hand, pressure on the pure water surface with the same area was measured to determine a difference between them for each value of DNA concentration, thus preparing a calibration curve as shown in FIG. 8.

Figure 8:
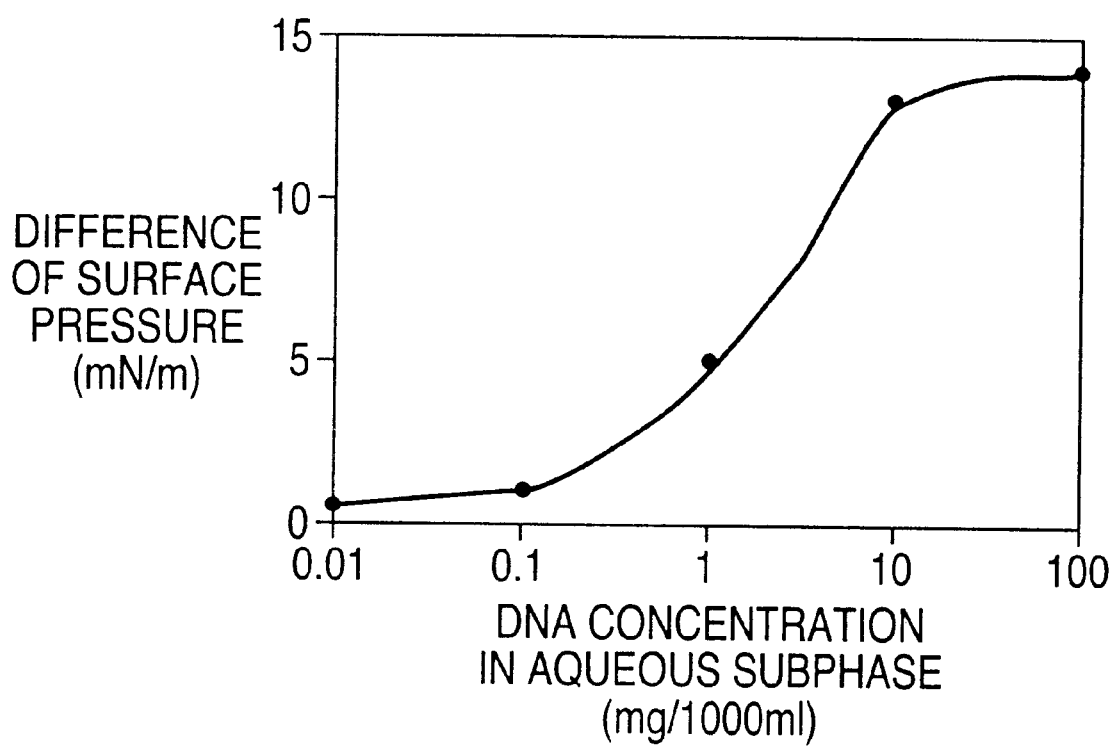
FIG. 8 illustrates changes in the difference in surface pressure depending upon concentrations of a nucleic acid polymer.

As is clear from FIG. 8, the difference in surface pressure was confirmed to exhibit a correlation with logarithm of DNA concentration within a range of DNA concentration of from 0.1 to 10 mg/1000 ml.

EXAMPLE 4

Figure 9:
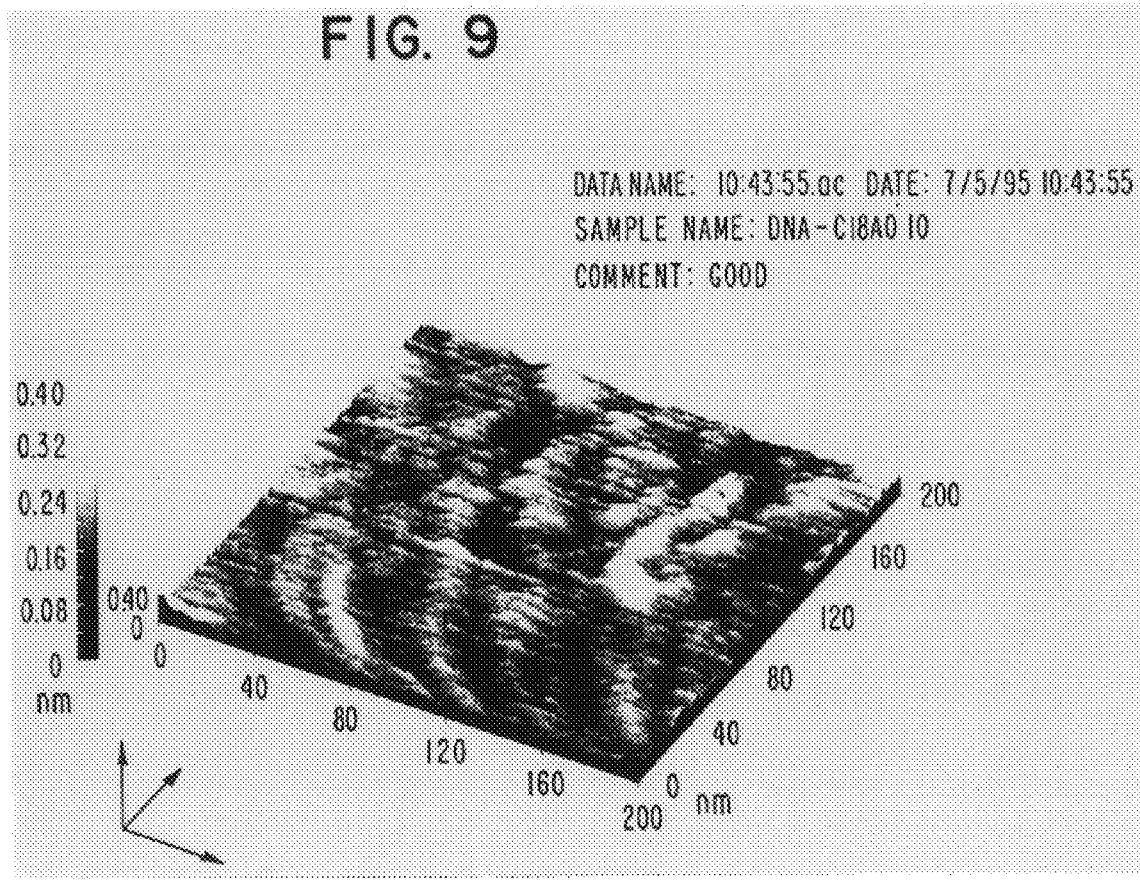
FIG. 9 is an atomic force microscopic image of an intercalator/DNA monolayer deposited on a mica substrate.
Figure 10:
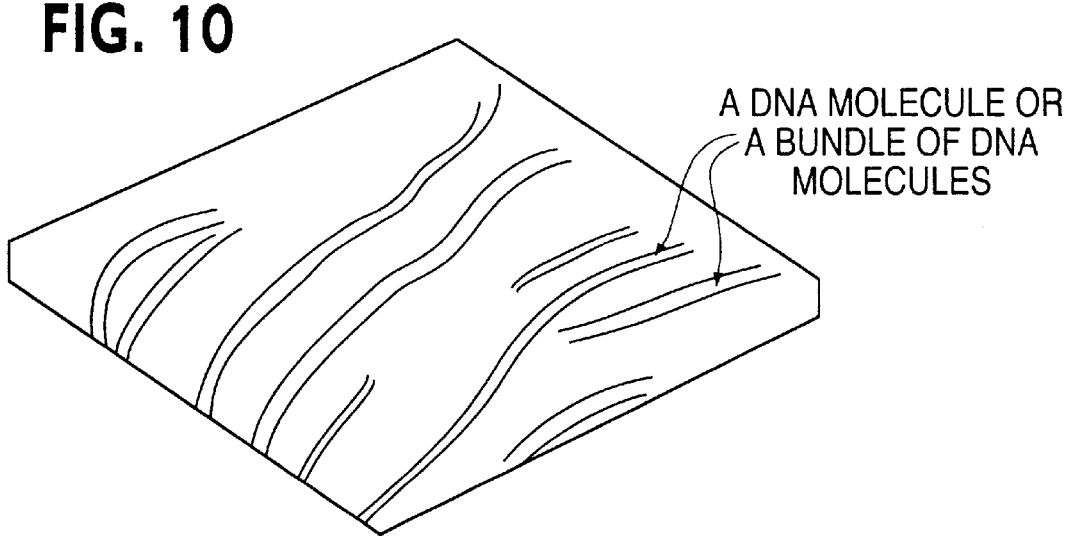
FIG. 10 is a schematic drawing of the microscopic image of FIG. 9.

An aqueous solution was prepared by dissolving a double helix DNA (extracted from salmon spermatozoon) in pure water, to a DNA concentration of 10 mg/1000 ml and a pH of 5.6. A chloroform solution of the surface-active intercalator of Formula 1 was spreaded onto the gas-water interface of this aqueous solution, and the interface was compressed while measuring the surface pressure by the same method under the same conditions as in Example 1. The compression was discontinued when the surface pressure reached 10 mN/m, and control was carried out so as to always keep this value of the surface pressure. A freshly cleaved mica substrate had previously been immersed vertically in the aqueous subphase of the apparatus. A single layer of a composite monolayer comprising the intercalator and the DNA was derposited on the substrate by pulling up this substrate vertically at a speed of 50 mm/minute. After air drying, the substrate surface was observed in AC mode (scanning area: 200×200 nm²) by the use of an atomic force microscope (NV2500, made by Olympus). The result is as shown in the microscopic image of FIG. 9 and the shematic drawing thereof of FIG. 10. The monolayer is compressed from right toward left in this image. Cords having a width of from 10 to 20 nm were observed in parallel sequence with a difference of 2 to 3 Å, and DNA molecules were found to be vertically oriented relative to the compression direction in bundles. It was confirmed from these results that it was possible to control two-dimensional orientation of a nucleic acid polymer by combination with the intercalator of the present invention. In addition, thus obtained nucleic acid polymer/intercalator monolayer or the monolayer deposited on a substrate, in which polymer molecules or bundles of the molecules are oriented in the same direction. will be used for a molecule devise such as micro-conductor, sensor and a tool for studying the orientation state of DNA or RNA.

Particularly, for example, Br— which is a conventional intercalator is water-soluble because of a short hydrophobic group as $C_{12}H_{25}$, so that development thereof on a gas-liquid interface only causes dissolution into the aqueous subphase, a no rise of surface pressure is observed even by compression. In the methods of the present invention described in the above-mentioned examples, therefore, it is essential to use, not a conventional one, but a surface-active intercalator modified by a hydrophobic group into an amphiphilic one.

What is claimed is:

1. A method for orienting nucleic acid polymers, which comprises spreading an amphiphilic intercalator containing a hydrophobic group on an aqueous solution containing nucleic acid polymers to intercalate said amphiphilic intercalator into said nucleic acid polymers, thereby orienting said nucleic acid polymers at a gas-water interface of the aqueous solution.

2. A nucleic acid polymer/intercalator monolayer comprising a monolayer of nucleic acid polymers which are intercalated with an amphiphilic intercalator containing a hydrophobic group, said hydrophobic group being an alkyl group expressed by $C_nH_{2n+1}$ ($n \geq 13$).

3. The nucleic acid polymer/intercalator monolayer of claim 2, which exists at a gas-water interface of an aqueous solution.

4. A nucleic acid polymer/intercalator monolayer of claim 2, which exists on a substrate.

5. The nucleic acid polymer/intercalator monolayer of claim 2, wherein the intercalator is acridine orange.

6. The nucleic acid polymer/intercalator monolayer of claim 2, wherein the hydrophobic group is an octadecyl group.

7. The nucleic acid polymer/intercalator monolayer of claim 2, wherein the amphiphilic intercalator containing the hydrophobic group is expressed by any one of the following formulae:

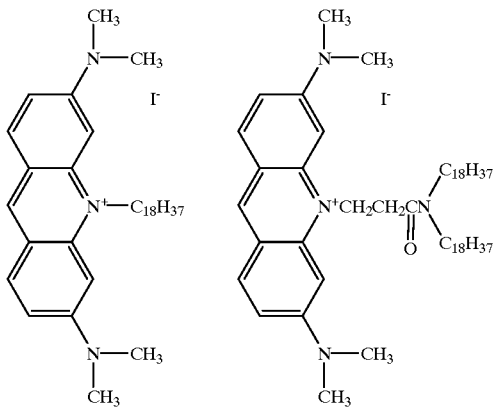

8. A nucleic acid polymer/intercalator monolayer obtained by a method comprising:

spreading an amphiphilic intercalator containing a hydrophobic group on an aqueous solution having a gas-water interface and containing nucleic acid polymers to intercalate said amphiphilic intercalator into said nucleic acid polymers and form a monolayer of said nucleic acid polymers and said amphiphilic intercalator at the gas-water interface, and isolating the monolayer from the gas-water interface of the aqueous solution to obtain the nucleic acid polymer/intercalator monolayer.

9. The nucleic acid polymer/intercalator monolayer of claim 8, which is deposited on a substrate after surface compression.

10. The nucleic acid polymer/intercalator monolayer of claim 8, wherein the hydrophobic group is an alkyl group expressed by $C_nH_{2n+1}$ ($n \geq 13$).

11. The nucleic acid polymer/intercalator monolayer of claim 8, wherein the intercalator is acridine orange.

12. The nucleic acid polymer/intercalator monolayer of claim 8, wherein the hydrophobic group is an octadecyl group.

13. The nucleic acid polymer/intercalator monolayer of claim 8, wherein the amphiphilic intercalator containing the hydrophobic group is expressed by any one of the following formulae:

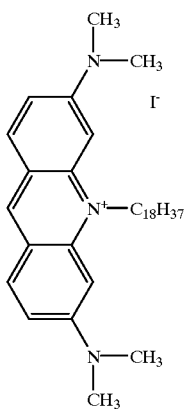
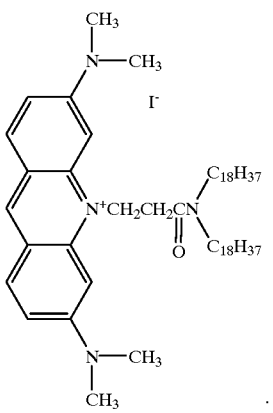

14. A method of making a nucleic acid polymer/intercalator monolayer comprising:

spreading an amphiphilic intercalator containing a hydrophobic group on an aqueous solution having a gas-water interface and containing nucleic acid polymers to intercalate said amphiphilic intercalator into said nucleic acid polymers and form a monolayer of said nucleic acid polymers and said amphiphilic intercalator at the gas-water interface, and isolating the monolayer from the gas-water interface of the aqueous solution to make the nucleic acid polymer/intercalator monolayer.

15. The method of making a nucleic acid polymer/intercalator monolayer of claim 14, wherein the hydrophobic group is an alkyl group expressed by $C_nH_{2n+1}$ ($n \geq 13$).

16. The method of making a nucleic acid polymer/intercalator monolayer of claim 14, wherein the intercalator is acridine orange.

17. The method of making a nucleic acid polymer/intercalator monolayer of claim 14, wherein the hydrophobic group is an octadecyl group.

18. The method of making a nucleic acid polymer/intercalator monolayer of claim 14, wherein the amphiphilic intercalator containing the hydrophobic group is expressed by any one of the following formulae:

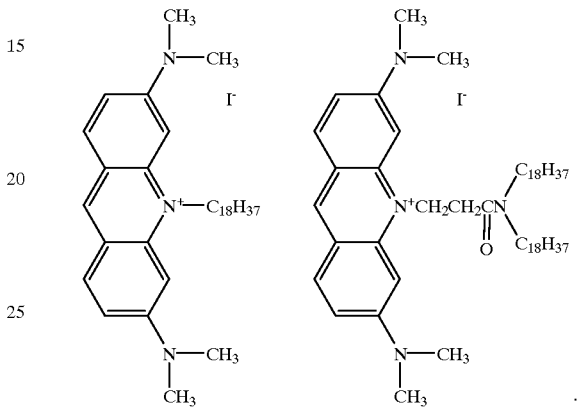

* * * * *